(12) United States Patent
Ng et al.

(10) Patent No.: US 7,118,626 B2
(45) Date of Patent: Oct. 10, 2006

(54) CRYSTALLIZATION CASSETTE FOR THE GROWTH AND ANALYSIS OF MACROMOLECULAR CRYSTALS AND AN ASSOCIATED METHOD

(75) Inventors: Joseph D. Ng, Huntsville, AL (US); Juan-Manuel Garcia-Ruiz, Granada (ES); Jose A. Gavira-Gallardo, Granada (ES); Mark Wells, Athens, AL (US); Greg Jenkins, Madison, AL (US)

(73) Assignee: University of Alabama in Huntsville, Huntsville, AL (US)

( * ) Notice: Subject to any disclaimer, the term of this patent is extended or adjusted under 35 U.S.C. 154(b) by 212 days.

(21) Appl. No.: 10/651,499

(22) Filed: Aug. 29, 2003

(65) Prior Publication Data

US 2005/0045094 A1    Mar. 3, 2005

(51) Int. Cl.
*C30B 7/02* (2006.01)

(52) U.S. Cl. .............................. 117/68; 117/69; 117/70; 422/245.1

(58) Field of Classification Search ............. 422/245.1; 117/68, 69, 70
See application file for complete search history.

(56) References Cited

U.S. PATENT DOCUMENTS

| | | | |
|---|---|---|---|
| 3,337,304 A | 8/1967 | Lorenzini | |
| 3,499,736 A | 3/1970 | Zwaneburg | |
| 4,755,363 A | 7/1988 | Fujita et al. | |
| 4,886,646 A | 12/1989 | Carter et al. | |
| 4,917,707 A | 4/1990 | Claramonte et al. | |
| 5,013,531 A * | 5/1991 | Snyder et al. | 117/223 |
| 5,078,975 A * | 1/1992 | Rhodes et al. | 117/206 |
| 5,096,676 A | 3/1992 | McPherson et al. | |
| 5,130,105 A | 7/1992 | Carter et al. | |
| 5,363,797 A | 11/1994 | Uenishi et al. | |
| 5,419,278 A | 5/1995 | Carter | |
| 5,552,127 A | 9/1996 | Asano | |
| 5,641,681 A | 6/1997 | Carter | |
| 5,643,540 A | 7/1997 | Carter et al. | |
| 5,861,306 A | 1/1999 | Pugh et al. | |
| 5,961,934 A | 10/1999 | Arnowitz et al. | |
| 6,039,804 A | 3/2000 | Kim et al. | |
| 6,060,028 A | 5/2000 | Yoneda et al. | |
| 6,174,365 B1 * | 1/2001 | Sanjoh | 117/68 |
| 6,267,935 B1 | 7/2001 | Hol et al. | |
| 6,409,832 B1 | 6/2002 | Weigl et al. | |
| 6,447,602 B1 | 9/2002 | Beswick | |
| 6,447,726 B1 | 9/2002 | Delucas et al. | |
| 6,468,346 B1 | 10/2002 | Arnowitz et al. | |
| 6,746,160 B1 * | 6/2004 | Takeuti et al. | 385/84 |
| 6,818,060 B1 * | 11/2004 | Stewart et al. | 117/68 |
| 2001/0027745 A1 | 10/2001 | Weigl et al. | |

(Continued)

OTHER PUBLICATIONS

Gavira et al., *Ab Initio* Crystallographic Structure Determination Of Insulin From Protein To Electron Density Without Crystal Handling, *Acta Cryst.*, Jul. 2002, 58, pp. 1147-1154.

(Continued)

*Primary Examiner*—Robert Kunemund
(74) *Attorney, Agent, or Firm*—Alston & Bird LLP

(57) ABSTRACT

The invention is a crystallization cassette and associated method for growing and analyzing macromolecular crystals in situ by X-ray crystallography. The cassette allows proteins (as well as other macromolecules) to be crystallized by the counter-diffusion method in a restricted geometry. Using this procedure, crystals can be adequately prepared for direct X-ray data analysis such that the protein's three-dimesional structure can be solved without crystal manipulation.

62 Claims, 11 Drawing Sheets

U.S. PATENT DOCUMENTS

| | | |
|---|---|---|
| 2002/0039472 A1* | 4/2002 | Takeuti et al. ............. 385/84 |
| 2002/0064485 A1 | 5/2002 | Delucas et al. |
| 2002/0100411 A1 | 8/2002 | Arnowitz et al. |
| 2002/0106318 A1 | 8/2002 | Delucas et al. |
| 2002/0122760 A1 | 9/2002 | Delucas et al. |
| 2002/0164653 A1 | 11/2002 | Downs |
| 2002/0164812 A1 | 11/2002 | DeLucas |
| 2002/0189529 A1 | 12/2002 | David et al. |
| 2002/0195046 A1 | 12/2002 | David et al. |
| 2003/0003036 A1 | 1/2003 | Rouleau et al. |
| 2003/0022383 A1 | 1/2003 | DeLucas |
| 2003/0022384 A1 | 1/2003 | DeLucas |
| 2003/0027348 A1 | 2/2003 | DeLucas et al. |
| 2003/0075101 A1 | 4/2003 | Weigl et al. |
| 2003/0096421 A1 | 5/2003 | DeLucas et al. |
| 2004/0139909 A1* | 7/2004 | Morris et al. ............. 117/2 |

OTHER PUBLICATIONS

Ng et al., Protein Crystallization By Capillary Counterdiffusion For Applied Crystallographic Structure Determination, Journal Of Structural Biology, 142, pp. 218-231, 2003.

* cited by examiner

CRYSTALLIZATION CASSETTE FOR THE GROWTH AND ANALYSIS OF MACROMOLECULAR CRYSTALS AND AN ASSOCIATED METHOD

FEDERALLY SPONSORED RESEARCH OR DEVELOPMENT

The United States Government may have rights in the inventions set forth herein as provided by the terms of Grant No. NCC8-243 awarded by the National Aeronautics and Space Administration.

BACKGROUND OF THE INVENTION

The recent deciphering of entire genomic sequences of different organisms, including humans, has resulted in a demand to decipher three-dimensional structures of protein gene products. Determining the structures of proteins may allow researchers to compile structural information that will facilitate predictions of function for almost any protein from knowing its coding sequences. Gaining a better understanding of protein structure and function may enable drug researchers to develop new drug treatments that target specific human, animal, and plant diseases. The human body alone has an estimated 52,000 different proteins. Determining the structures to atomic resolution for all these proteins is a daunting challenge, at best. X-ray crystallography currently offers one method to achieve this goal and is the only method to date for determining macromolecules greater than 35,000 Daltons.

Today, advanced recombinant DNA methods, systematic approaches for protein crystallization, and highly developed X-ray diffraction instruments and procedures contribute to determining protein structure. The limiting step in protein structural determination is the ability to obtain protein crystals that are suitable for X-ray diffraction. Suitable crystals should be able to diffract to atomic resolutions greater than 3 Angstroms with reflections that can be readily indexed.

The process for obtaining crystals suitable for X-ray diffraction normally is divided into four discrete steps. The first step includes determining conditions for initial protein crystallization. There are numerous factors influencing crystal formation, which include: pH, ionic strength, temperature, gravity, and viscosity, to name but a few. Second, the initial crystallization conditions are optimized to produce crystals that are suitable for X-ray diffraction. This step entails making minute adjustments to the many crystallization parameters to produce the highest quality crystal.

In the third step, the crystals are treated with a cryoprotectant solution so that the protein crystal will tolerate supercooled conditions. Protein crystals are very sensitive to X-ray radiation and therefore data collection must be performed under super cooled conditions. During this step, the researcher typically tests the crystal in a variety of cryogenic solutions at different concentrations and soak times.

In the final step, strong X-ray scattering atoms are required for ab initio phasing. Atoms such as sulfur or metal ions are intrinsic to most proteins and are often used for crystallographic phasing by using the atoms' anomalous signals. However, halides or heavy metals provide much higher X-ray scattering signals for effective phasing and they are typically incorporated into the protein in an invasive manner. This step usually requires rigorous testing to find appropriate scattering atoms that can be isomorphously incorporate into the crystal without damaging the crystalline order.

Typically, the third and fourth steps require the researcher to manually transfer protein crystals between different solutions followed by mounting the crystal on cryoloops for X-ray analysis. These steps require that the researcher delicately handle the crystal because any over excursion of force or mishandling could damage the crystal. Current methods for growing and analyzing protein crystals are time intensive, often fail to produce useful crystals, and require that the researcher use extreme care when handling the crystals.

From the foregoing, it should be readily apparent that obtaining protein crystals and their subsequent preparation for X-ray analysis is a very time consuming and limiting step in determining protein structure. Consequently, more efficient methods are needed for growing protein crystals suitable for analysis.

BRIEF SUMMARY OF THE INVENTION

The invention is a crystallization cassette that is useful for crystallizing biological molecules. Although the invention is described for crystallizing proteins for X-ray analysis, it should be understood that other macromolecules such as nucleic acids and viruses are also be applicable. The cassette provides a technique that incorporates all four protein crystallization steps and the step of X-ray analysis into a single apparatus. All steps are performed in situ so that it is not necessary for the researcher to manually manipulate the crystals. The cassette is adaptable for high-throughput crystallography so that the process can be performed under automated conditions.

The cassette has a top section and a lower member. The top section contains multiple capillary tubes that extend downward from a housing member through passageways contained in a stabilizing member. The tips of the capillaries extend below the stabilizing member. The lower member contains multiple cavities that contain a precipitating solution, cryoprotectant solution and a scattering atom component. Each cavity corresponds to a single capillary.

A pierceable layer seals the desired solutions and scattering atom component within the cavities. A drop of protein sample is placed on the pierceable layer above each cavity. The top section is attached to the lower member so that the capillary tips contact the protein samples.

The protein samples are taken into the capillaries by capillary action. After the protein solutions have filled the capillary tubes to the desired levels, the lower member slides towards the stabilizing member so that the capillary tips penetrate the pierceable layer and the tips contact the solutions contained within the cavities. At this time, the protein solutions and the solutions contained within the cavities counter-diffuse against each other and a supersaturation wave is formed within each capillary. Protein crystals begin to form as the superstaturation wave moves through the capillary.

During the counter-diffusion process, a spatial-temporal gradient is formed along the length of the capillary tube. As a result, varying supersaturation conditions that lead to crystal growth are simultaneously present in the capillary. Each cassette will greatly improve the chances of obtaining crystals that are suitable for X-ray analysis. Thus, the invention is a significant step forward in achieving the goal of solving the structures for thousands of proteins.

In one embodiment, the housing member is designed to allow each capillary tube to pivot upwardly so that a capillary's tip extends outwardly away from the cassette. Each capillary tube can be extended away from the cassette at an angle that varies anywhere from about 0 to 180 degrees. The outward extended capillary is placed in an X-ray beam for data collection. The capillaries are analyzed while they are in the cassette or, alternatively, they can be removed for individual analysis.

The capillary tubes are constructed of an amorphous material that is suitable for X-ray analysis. This is usually a quartz or amorphous polymer. The size of the capillary tube may vary depending upon use and desired crystal size. The diameter can range anywhere from about 0.05 mm to 1 mm, with capillary tubes having diameters less than about 0.3 mm obtaining the best results.

The size and shape of the cassette can vary depending upon the size of the capillaries or the number of capillaries that are used. A cylinder shape normally offers the most efficient space packing geometry.

Thus, the invention provides among other things, an apparatus for growing, cryoprotecting, incorporating scattering atoms, and analyzing macromolecular crystals in situ for direct protein structure determination.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

DETAILED DESCRIPTION OF THE INVENTION

The invention now will be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements. Like numbers refer to like elements throughout.

Figure 1:
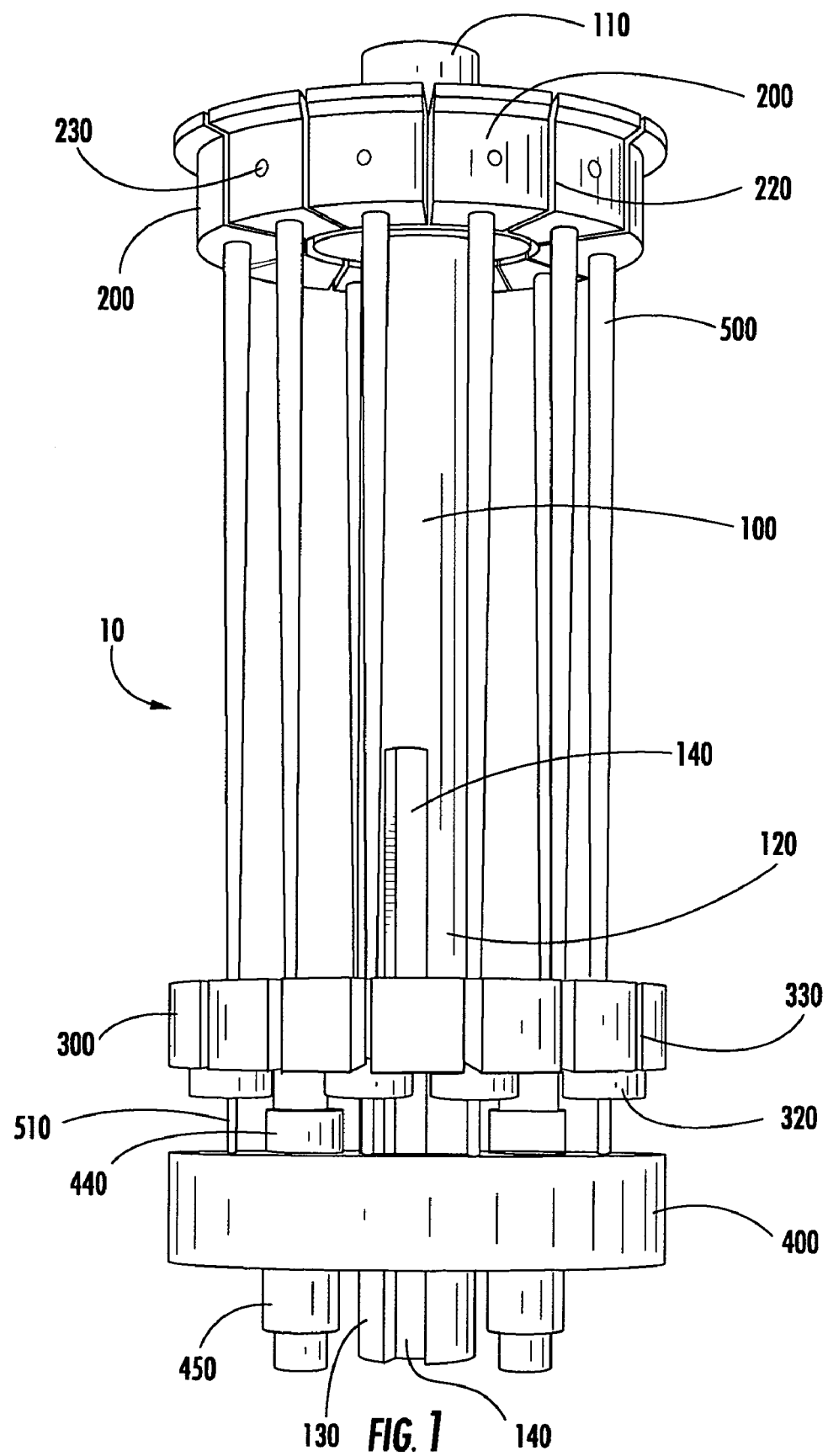
FIG. 1 is a perspective view of a crystallization cassette that has been fully assembled.

Referring more specifically to the drawings, for purposes of illustration, but not of limitation, there is shown in FIG. 1 a form of the crystallization cassette referred to generally as 10. FIG. 1 illustrates a fully assembled cassette having a support member 100, a housing member 200, a stabilizing member 300, a precipitating reservoir member 400, and a plurality of capillary tubes 500. With reference to FIG. 8, reference number 800 broadly designates a second form of the cassette. FIG. 8 illustrates a crystallization cassette having a support member 814, a housing member 822, a stabilizing member 816, a precipitating reservoir member 900, and a plurality of capillary tubes 850.

Referring back to the first form of the cassette 10, FIG. 1 illustrates a cassette having a support member that is a shaft 100 having a top portion 110, a middle portion 120 and a lower portion 130. The housing member 200, also termed the upper member, is joined to the top portion 110 of the shaft. The stabilizing member 300, also termed the middle member is joined to the shaft proximate the middle portion of the shaft 120. The precipitating reservoir member 400, also termed the lower member, is located near the shaft's lower portion 130.

As depicted in FIG. 1, the upper member 200 is joined to the shaft's top portion 110. With reference to FIGS. 1 through 4, the upper member 200 is depicted as having a plurality of capillary tubes 500 extending downwardly from its lower surface 270 at 240.

Figure 2:
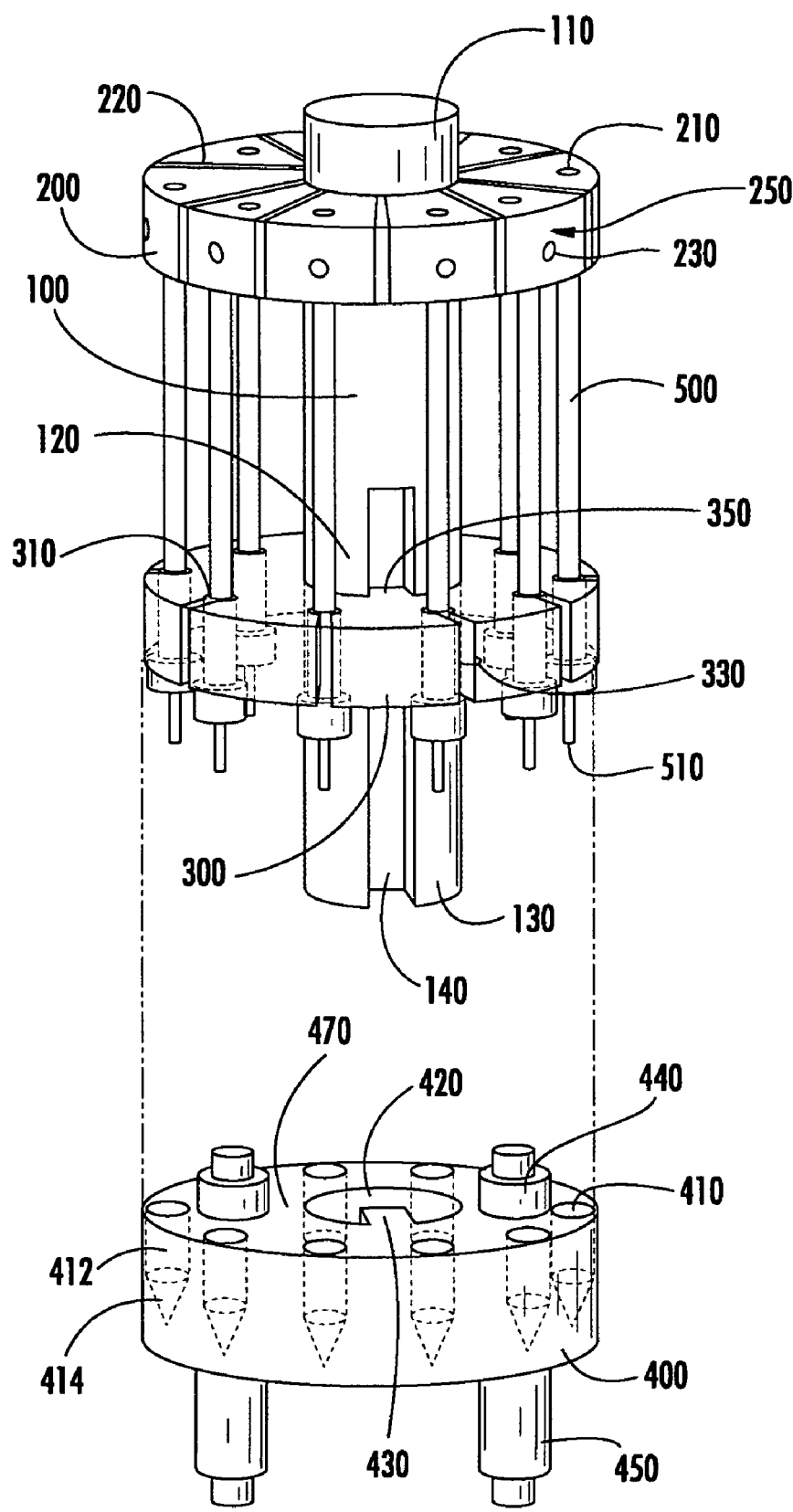
FIG. 2 is a perspective view of the of the cassette shown in FIG. 1 having the lower member separated from the shaft.

The proximal ends of the capillary tubes are joined to the upper member at 240. The tubes 500 extend downwardly from the upper member through passageways 310 disposed in the middle member 300. As illustrated in FIG. 2, the capillary tubes' distal ends 510 extend downwardly below the middle member and are positioned above the cavities 410 on the lower member 400.

Figure 4A:
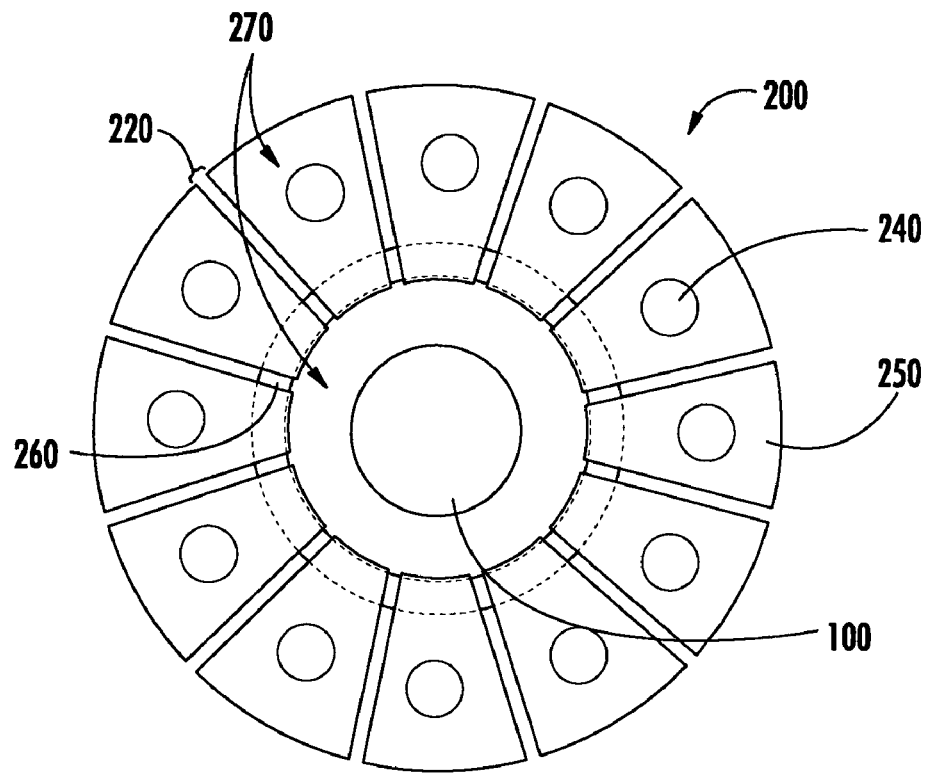
FIG. 4a is an underside view of the upper member.
Figure 4B:
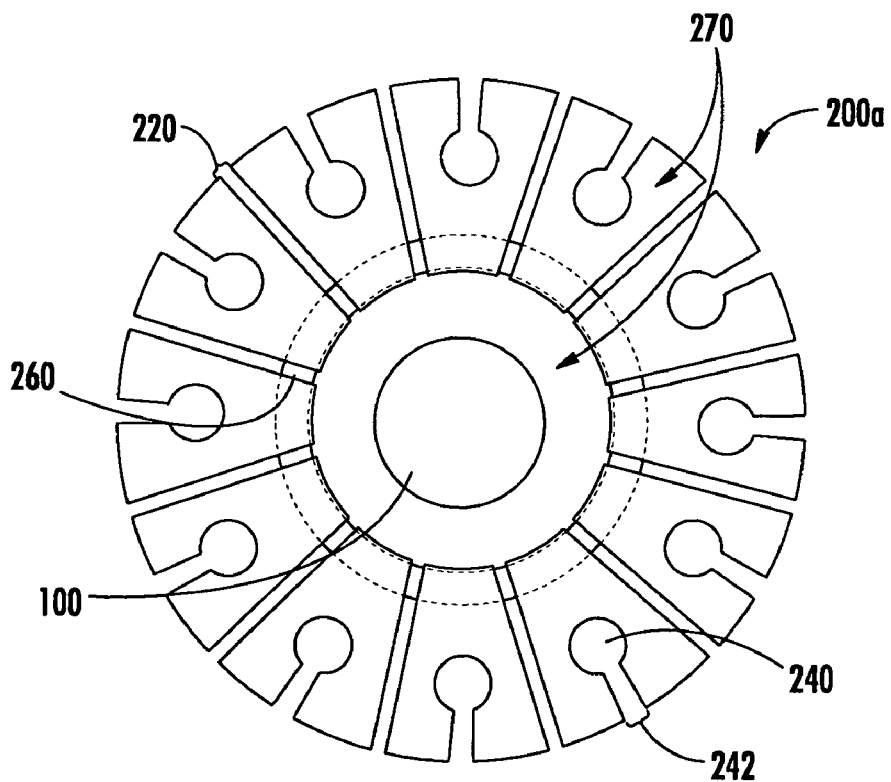
FIG. 4b is an underside view of the upper member having side channels.

With reference to FIGS. 4a and 4b, the upper member's lower surface 270 is illustrated having a plurality of openings 240 through which the proximal end of the capillary is inserted. After inserting a capillary tube into an opening 240, a bonding agent, such as an adhesive, can be inserted through the upper openings 210 on the upper member's top surface or through the outer openings 230 that are disposed on the outer edge (FIG. 2). The bonding agent secures the capillary tubes within the upper member. However, it should be recognized that it is not necessary to use a bonding agent and that the capillary tubes could be frictionally joined to the upper member or non-permanently stabilized by vacuum grease or modeling clay.

FIG. 4b illustrates an alternative method of attaching the capillary tubes to the upper member. As shown in FIG. 4b, each capillary opening is connected to a channel 242. Manual pressure is applied to the channel's sides to increase the size of the channel until the distance is great enough to slip the proximal end of a capillary tube through the channel and into the opening 240. Once the capillary tube is positioned in the opening, manual pressure is released and the capillary tube is fit tightly within the opening. This method of installing the capillary tubes allows the tubes to be easily removed and replaced.

Figure 3A:
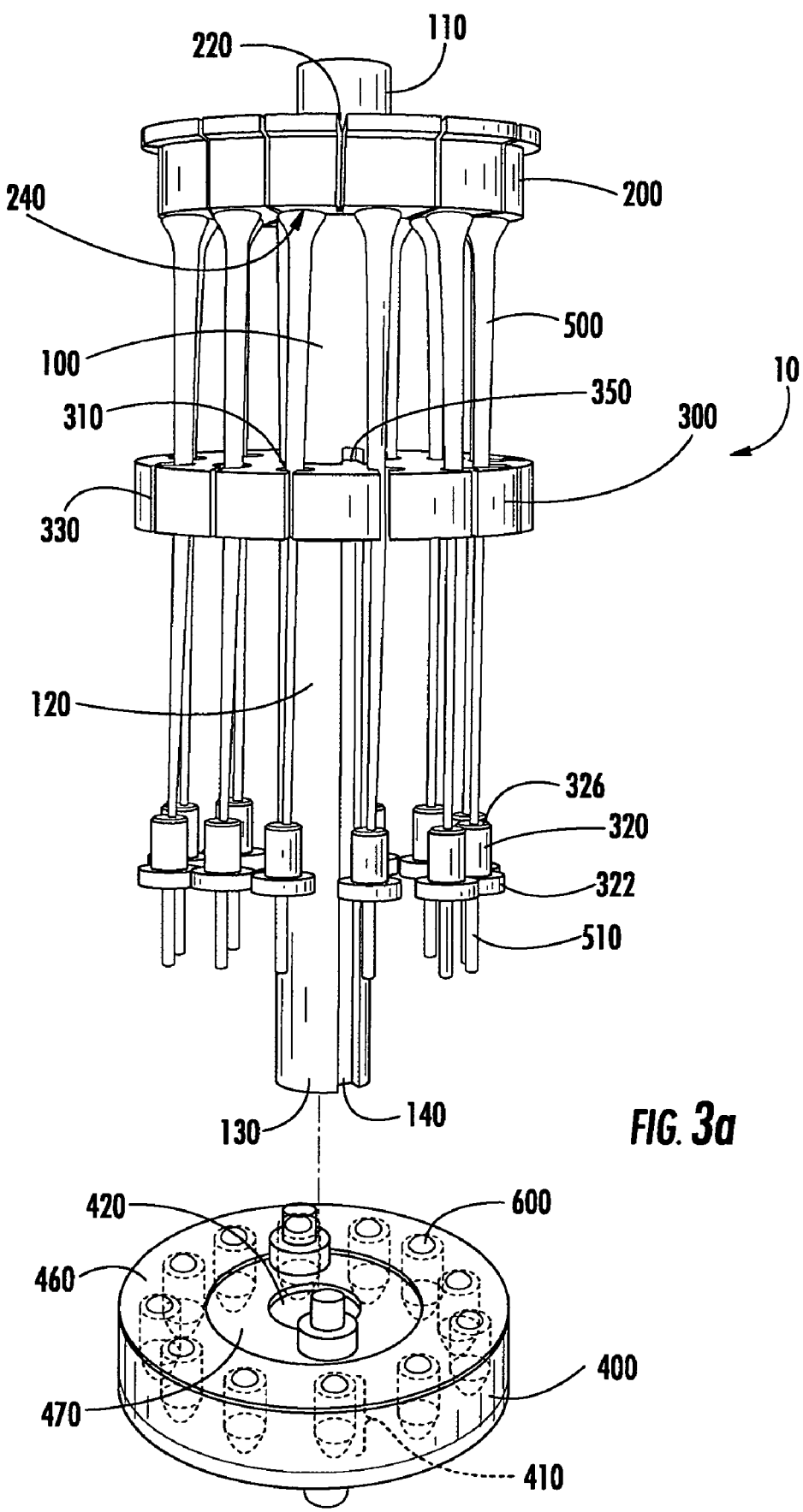
FIG. 3a is a perspective side view of the cassette shown in FIG. 2 having the middle member disengaged from the ferrels.
Figure 3B:
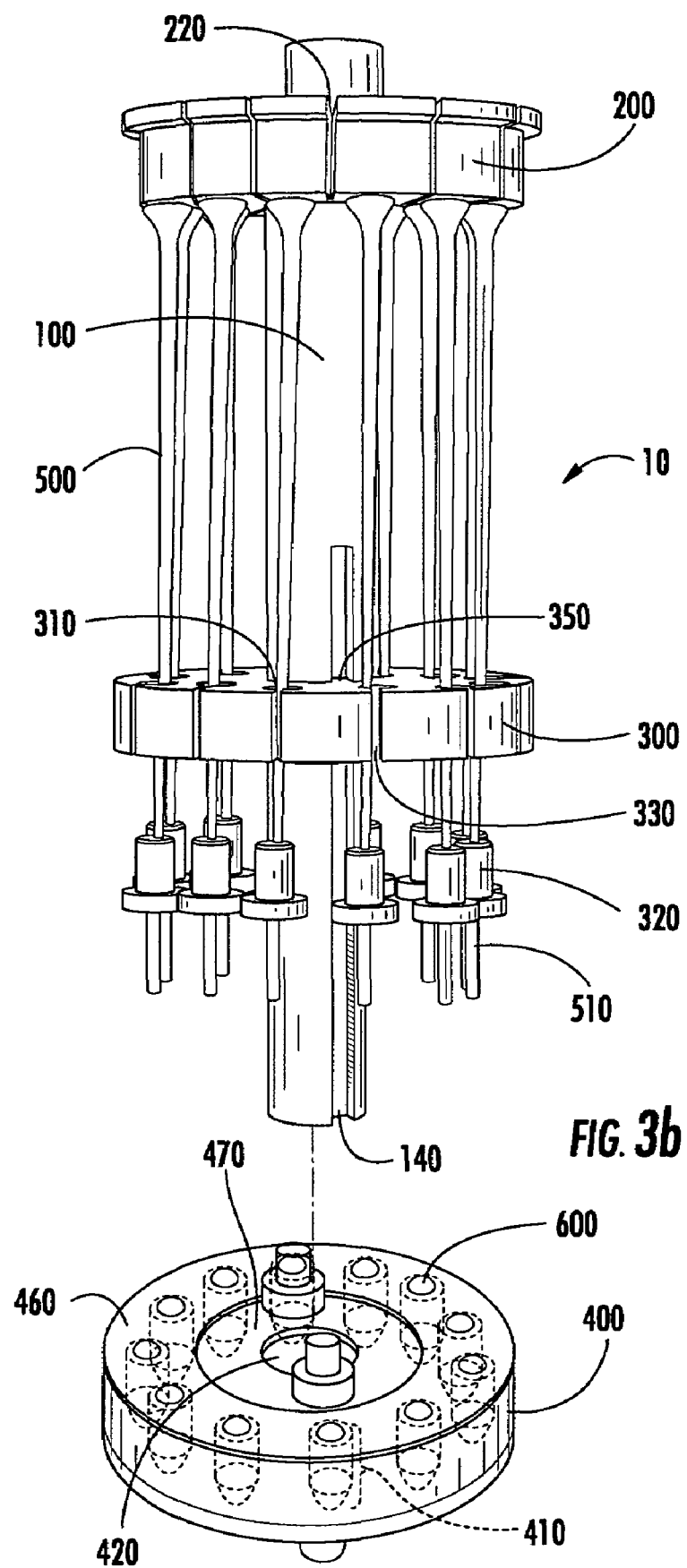
FIG. 3b is a perspective view of the cassette shown in FIG. 2 illustrating that the middle member can slide along the shaft.
Figure 3C:
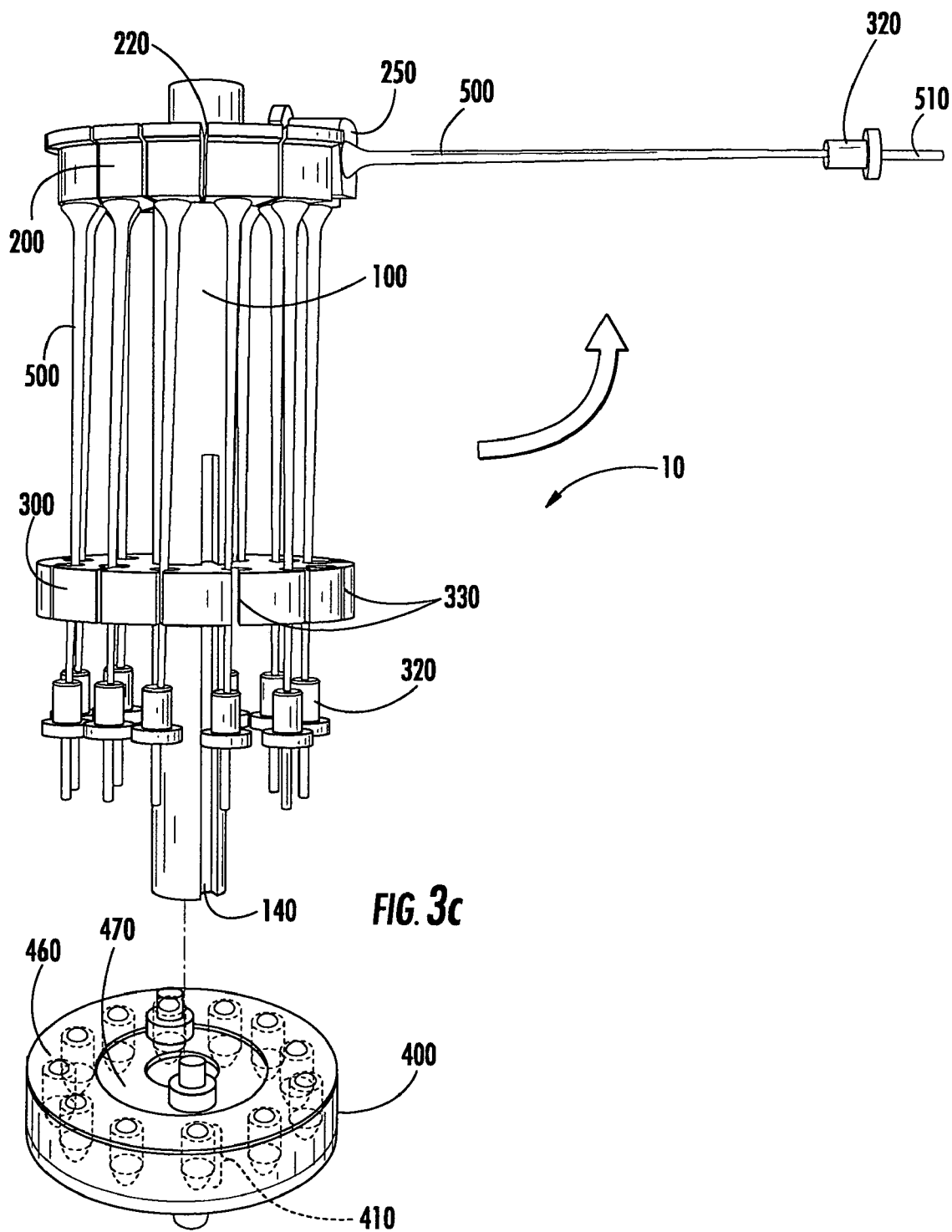
FIG. 3c is a perspective view of the cassette shown in FIG. 3b having a capillary tube in an outwardly extended position.

As shown in FIG. 3c, each capillary tube may extend outwardly from the crystallization cassette. The upper member 200 has a plurality of capillary housing members 250 that are each independently pivotable. As shown in FIGS. 1 through 4, the upper member has a plurality of narrow separations 220 that separate the capillary housing members from each other. These narrow separations allow the capillary housing members to pivot independently from each other. Near the center of the upper member, proximate to the shaft 100, the upper member has an area of decreased thickness. This area of decreased thickness functions as a hinge so that the capillary housing members are able to pivot upwardly. As shown in FIGS. 4a and 4b, the hinge 260 is the area represented between the dashed lines.

As should be apparent, hinge thickness will change the angle degree to which the capillary tube is free to pivot. The capillary tube is possibly able to pivot anywhere from about 0 to 180 degrees, with an angle of about 90 degrees being somewhat more typical. The hinge thickness range is typically from about 0.010 to 1.0 mm.

Capillary tubes that extend outwardly from the cassette offer a significant advantage. This allows the cassette to be analyzed in an automated system, which will greatly increase the speed and efficiency at which crystals are screened and analyzed. In practice, the outwardly extended capillary is extended and positioned into an X-ray beam.

The upper member can be joined to the shaft in a variety of different ways. For example, by way of illustration and not limitation, the upper member can be adhesively bonded to the shaft; the shaft or upper member may have a taper that allows the upper member and the shaft to be frictionally fit together; or a set screw could secure the upper member. Alternatively, the shaft and upper member could be fabricated using an injection molding process so that they have a unitary body.

As shown in FIG. 1, the middle member 300 is disposed near the shaft's middle portion 120. The middle member has a channel that can receive the shaft so that the middle member can slide along the shaft. With reference to FIG. 3a through FIG. 3c, the middle member is shown positioned at various locations on the shaft. The middle member has a plurality of passageways 310 that extend longitudinally from the middle member's upper surface to its lower surface. Each capillary tube 500 has a corresponding passageway 310. The passageways secure the capillaries in the middle member, while at the same time allowing the capillaries' bodies to slide freely through the middle member as the middle member is moved on the shaft.

A ferrel 320 prevents the capillaries from having too much free movement within the passageways. The ferrel 320 is disposed near the distal end 510 (tip) of the capillary tube. As the middle member is slid downwardly into a locked or engaged position, the ferrels 320 enter the passageways 310 to securely hold the capillary tubes. Typically, the ferrel has a body 320, a base 322, and a beveled upper edge 326. The base typically has a diameter greater than the diameter of the ferrel's body 320. This prevents the base from entering the passageway 310, and thereby stops the middle member's movement towards the lower member. As shown in FIG. 2, the ferrel's body 320 slips into the passageway 310 and the base 322 remains outside the passageway. The upper edge of the ferrel has a bevel 326 to assist in seating the ferrel into the passageway. Although not illustrated, it should be understood that the middle member's lower surface at the passageways' edges could also be beveled.

The figures and above text describe a ferrel having a substantially round body. The primary function of the ferrels is to stabilize and steady the capillaries within the middle member, and as such, it should be recognized that a variety of different structures could perform the same function, although not necessarily with equivalent results. For instance, a square ferrel and passageway could stabilize the capillary tubes. Alternatively, a piece of tape or cushioning material, such as a foam, attached to the distal ends or located within the passageways could provide stabilization.

The illustrations show that each passageway 310 has a corresponding channel 330, which extends laterally from the outer edge to the passageway. The channels, similar to the passageways, extend longitudinally from the middle member's upper surface to its lower surface. When the middle member is pushed upwardly along the shaft, the ferrels are disengaged from the passageways (FIG. 3a). At this position, the capillary tubes fit rather loosely within the passageway. The channel 330 allows the broadside of a capillary tube's body to pass from the passageway 310, through the channel 330, and into an outwardly extended position (FIG. 3c).

Figure 5:
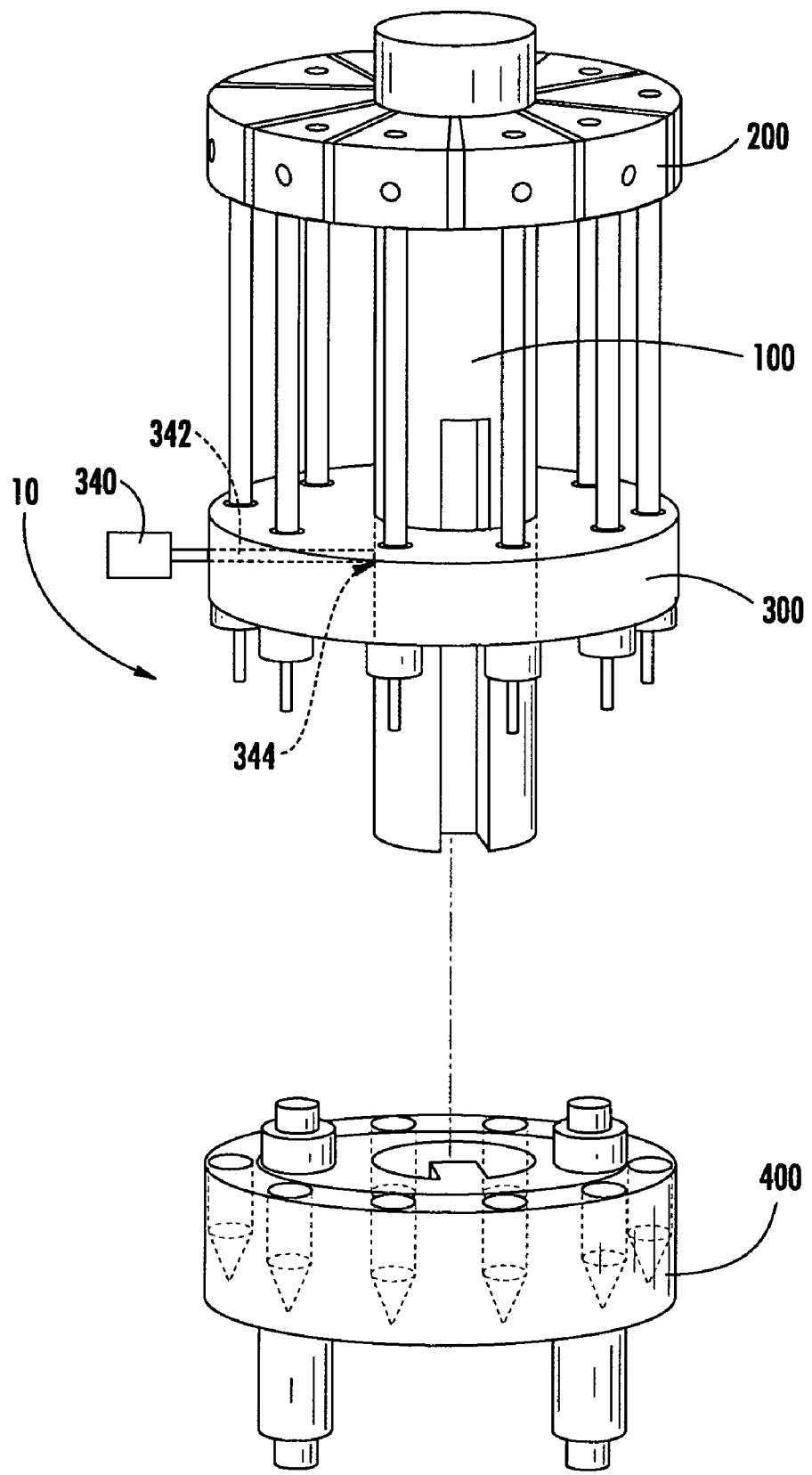
FIG. 5 is a perspective view of the cassette shown in FIG. 2 having a positioning pin.

To secure the middle member to the shaft and prevent its movement, the cassette may have a positioning lock. As shown in FIG. 5, a positioning pin 340 or set screw is inserted into a positioning channel 342 that extends laterally through the middle member in a direction that is substantially perpendicular to the shaft. The shaft has a corresponding recess into which the pin is insertable at 344. The recess is located on the shaft at a point that corresponds to the positioning channel's horizontal location and places the middle member in the desired vertical orientation along the shaft. Typically, the desired vertical orientation between the middle member and the shaft is when the passageways are securely fit over the ferrels (FIG. 2). Alternatively, the middle member could be secured in a desired location by a taper that is formed on the shaft or within the middle member's channel. It should be understood that securing the middle member's location along the shaft's axis is not limited to the above recited methods and a variety of different techniques could be used.

As stated above, the lower member is disposed on the shaft proximate to its lower portion. Similar to the middle member, the lower member also has a channel for receiving the shaft. As shown in FIGS. 3 and 4, the second channel 420 is disposed near the lower member's center. The lower member has an upper surface 470 that faces the middle member. A plurality of cavities 410 are disposed on the surface 470. Each cavity 410 is aligned with, and, corresponds to a capillary tube.

While in use, the cavities 410 act as reservoirs to contain the precipitating solution, which can also include cryoprotecting agents, heavy X-ray scattering atoms or any other additives. The bottoms of the reservoirs are layered with a sealant that is inert to the solutions and additives. The solutions are added individually or are pre-mixed and then deposited in the cavity. The cryoprotecting agents, heavy atoms and other additives can be initially mixed together or added in sequence during the crystallization process. As illustrated in FIG. 2, the cavities 410 have a lower portion 414 and an upper portion 412. Typically, a capillary sealant material, such as wax or clay, is disposed in the lower portion. The various illustrations depict a lower portion 414 that has a conical shape, but it should be understood that it is not necessary for the lower portion to have any particular shape and a flat surface would suffice.

The cavities upper portions 412 are filled with the various solutions for crystallization, as described above. The size of the cavities can be varied depending upon the size of the capillaries. Typically, capillaries having diameters from about 0.05 mm to 0.3 mm would have reservoirs containing volumes from about 5 to 50 microliters respectively. However, it should be recognized that other volumes could be useful, although not necessarily with equivalent results. After the cavities are filled, a pierceable layer 460 is placed on the surface 470 to seal the cavities.

In an alternative arrangement, the cavities are subdivided into two or three layers. In this arrangement, a second pierceable layer separates the cryoprotectant and precipitating solutions. The lower layer contains the capillary sealant. The middle layer is deposited above the sealant layer. The middle layer contains the cryoprotectant solution and, if desired, the scattering atom component. The upper layer contains the precipitating solution and, if desired, the scattering atom component. The division between the layers is created in several ways. One method is to physically add the second pierceable layer to the cavities to create the separation. Alternatively, the second pierceable layer is added during the manufacturing or assembly process. Under this arrangement, the lower member is made from an upper and lower section. The lower section, containing the cavities' lower and middle layers are filled with the sealant and a pre-selected cryoprotectant and scattering atom component. Thereafter, the second pierceable layer is placed on the lower section to seal the cavities. Next, the upper section is joined to the lower section to complete the assembly process. The assembly process can be completed within the lab or at the assembly plant.

It is envisioned that the lower members 400 can be pre-loaded at an assembly plant with various sealants, cryoprotectant solutions, precipitating solutions, and scattering atom components. A researcher may choose from a variety of pre-loaded lower members. Having pre-loaded lower members may also greatly enhance the efficiency and speed at which different protein crystallization conditions are screened. Additionally, pre-loaded lower members are ideally suited for high-throughput crystallization methods.

Figure 6A:
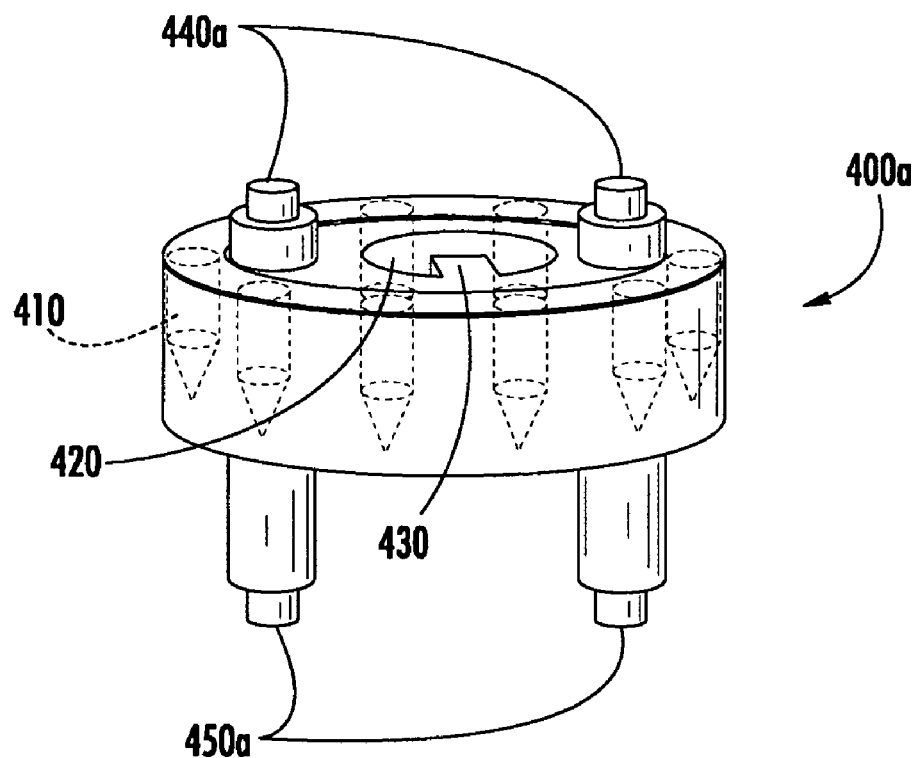
FIG. 6a is a perspective view of the lower member having a depth control stop.
Figure 6B:
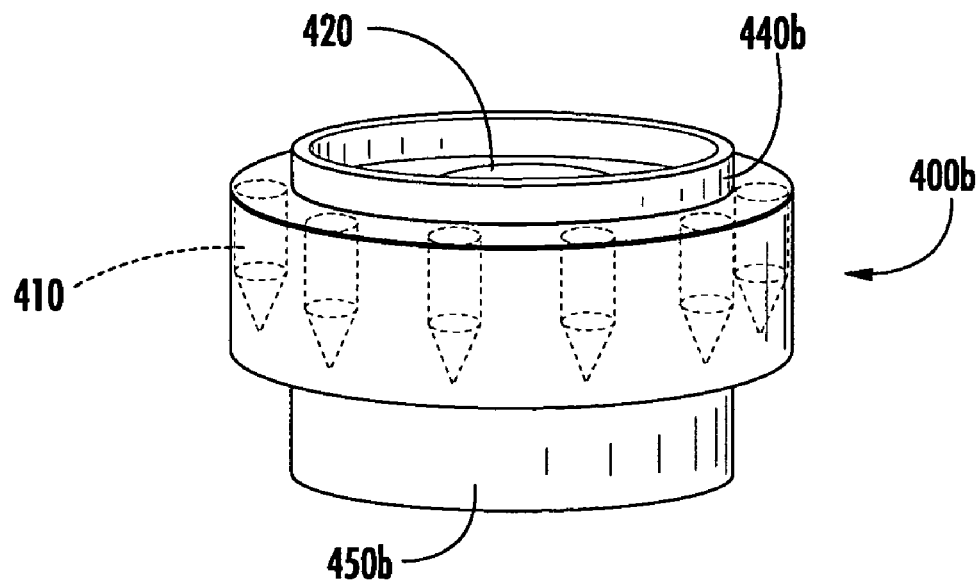
FIG. 6b is a perspective view of the lower member having an alternative form of the depth control stop.

With reference to FIGS. 6a and 6b, a capillary depth stop control is illustrated. The depth stop control functions to limit the lower member's upward movement as it slides along the shaft. Limiting the upward movement helps to ensure that the distal ends of the capillaries are not damaged by contact with the lower member. FIG. 6a illustrates a depth stop control that has two pairs of posts (studs) on opposite surfaces of the lower member. The upper studs 440a extend outwardly from the upper surface 470 at an angle that is substantially perpendicular to the surface. The lower studs 450a, similar to the upper studs, extend outwardly from the lower surface at an angle that is substantially perpendicular to the lower surface. As shown in FIG. 6a, the upper stud 440a height is different than the height of the lower stud 450a.

The depth control stop may come in a variety of different arrangements and orientations. For instance, as illustrated in FIG. 6b, the depth stop controls may be a unitary structure, such as rings 440b, 450b that project outwardly from the upper and lower surfaces. Alternatively, a removable pin or series of pins positioned on the shaft could function as a depth control stop. The pin(s) could be removed after completion of each step, thereby allowing the lower member to move along the shaft to the next desired position.

In an automated or manually operated system it may be sufficient to have a single depth control stop. In an automated system, the system would reposition the lower member a controlled distance at pre-determined intervals. The single depth control stop would prevent the capillary tips from contacting the cavities' bottoms. However, it should be recognized that having multiple depth control stops could be desirable or necessary depending upon experimental need.

In a cassette having two depth control stops on opposite surfaces, the lower stud 450a and upper stud 440a work cooperatively. In the first step, the lower member's lower surface is positioned on the shaft facing the middle member. Drops of protein sample are deposited on this lower surface in alignment with the capillary tubes. The lower stud 450a allows the capillary tips to contact protein samples deposited on the lower surface, but prevents the tips from contacting the surface. After the protein samples have filled the capillaries, the lower member is removed from the shaft and then reinserted onto the shaft so that the lower member's upper surface 470 is facing the middle member. Thereafter, the upper stud 440a prevents the tips from contacting the cavity through the remaining crystallization steps.

As shown in FIGS. 1 through 6, the shaft has a keyway 140 that extends along its vertical axis from the bottom portion towards the top portion. The middle portion and the lower portion each have a corresponding key 350, 430, respectively. The keys are adapted to slide within the keyway so as to prevent the middle or lower members from rotating around the shaft, which would place the passageways and cavities out of alignment with their respective capillary tubes. Alternatively, the shaft could have a key and the middle and upper members a keyway. It should be recognized that changing the geometric shape of the shaft and corresponding channels, such as to a square, would also prevent rotation about the shaft.

As illustrated in FIG. 1, the crystallization cassette 10 has a general cylindrical shape with the upper, middle, and lower members being discs. The cylindrical shape of the crystallization cassette 10 normally provides for the most efficient packing of capillary tubes. It should be recognized that the cassette could have a variety of different sizes and shapes. As illustrated in FIG. 3, the cassette 10 has 12 capillary tubes evenly spaced around the shaft. Changing the overall size of the cassette will allow the user to vary the number of capillary tubes that are present on the cassette. For instance, the larger the cassette, the more capillary tubes that can be placed in the cassette, and the opposite is equally true for a smaller cassette.

The cassette can be fabricated to be useful with a variety of different capillary tubes. Typically, the capillary size can range from about 0.05 mm to about 1 mm in diameter. Capillary tubes having diameters about 0.3 mm or less usually produce the best results. Larger capillaries can be used, but as the capillary diameter increases, the convective forces present within the capillary also increase. If it is desirable to use capillaries larger than 0.3 mm, a gel can be used to minimize convective flow within the capillary. Commonly used gels for macromolecular crystallization include agarose, silica gels, and polyacrylamides. The capillary tubes are usually made of quartz because of its amorphous qualities. Other materials may be used provided that they are amorphous or near amorphous and do not contribute to experimental diffraction.

The top section of the cassette, including the shaft, upper member, middle member, and capillary tubes can be fabricated as a single unitary structure through the use of injection molding. Materials for manufacturing the cassette and the capillaries include, without limitation, quartz, acrylic poly(methly methacrylate), polystyrene, mylar polycarbonate, CR 39, copolymers of styrene and poly(methly methacrylate), and derivatives or combinations of the aforementioned materials.

The lower portion 414 of the cavity is loaded with a capillary sealant that is suitable for sealing the capillary tubes' distal ends. Typically, the sealant is a soft wax or clay. However, other sealants could be used to seal the capillaries, although not necessarily with equivalent results.

After depositing the sealant in the cavities lower portion, the precipitating solution, cryoprotectant solutions, and scattering atom component are deposited in the cavities' upper portions 412. The solutions are either premixed or added individually to the cavities.

The precipitating agent most commonly contains salts (e.g. ammonium sulfate, sodium chloride or sodium citrate at concentrations of about 2–3M), alcohols (e.g. ethanol, proponal, methylpentanediol at concentrations of about 35–75%), or different forms of polyethylene glycol (PEG) (e.g. PEG 4000, 6000, 8000 concentrations between 15–50%) in a buffered media. The volume of precipitating solution (including any additional additives) placed into the cavities can be as little as the equivalent volume of the protein solution contained within the capillary.

Most protein crystals are very sensitive to X-rays and will not survive the X-ray exposure that is necessary for data collection. As a result, the crystals should be super-cooled without allowing the solvent content to go through an ice transition before X-ray analysis. Typically, this is accomplished by subjecting the crystal to a stream of cryogenic vapor (with temperatures around −150 to −170 C.), such as that from liquid nitrogen. For the sake of simplicity, the supercooled crystals will be also referred to as frozen crystals. In order for the crystal to endure the cooling process it is treated with a cryoprotectant prior to freezing. The cryoprotectant solution should protect the crystal while still sustaining its ability to diffract X-rays. Examples of cryoprotectants include glycerol, multiple alcohols, polyethylene glycols, oils, and even Indian cooking butter. Useful oils are typically composed largely of glycerides of the fatty acids, such as oleic, palmitic, stearic, and linolenic. Other chemical substances can be used provided that they sufficiently protect the crystal's structure during freezing, there is no resulting interference with crystal nucleation, and the crystal's ability to diffract X-rays is not adversely affected.

In order to grow protein crystals that are adequate for ab initio phase determination it is necessary to find a strong scattering atom that is intrinsic to the protein or to incorporate a derivative scattering atom, such as a heavy metal or halide. Bromide and iodide are halides that have been shown to be useful for diffusing into protein crystals and have been successfully used in crystallographic phasing. The anomalous X-ray scattering signals of halides are strong enough to provide phase information for X-ray crystallography, and as such, are usually useful for incorporation into the protein.

After the cavities are filled with the sealant and solutions, a pierceable layer 460 is placed over the cavities to seal them. The pierceable layer functions as a membrane to seal the solutions in the cavities while at the same time allowing the capillaries' distal ends to penetrate and enter the cavity. Suitable materials for the pierceable layer include, without limitation, latex, plastic plugs, waxes, agarose, or fracture ease.

Next, a drop of protein solution is deposited on the pierceable layer in a position that is directly above each cavity. The volume of protein solution deposited above each cavity will vary depending upon capillary size. It is expected that a capillary that is about 0.3 mm or less in diameter requires a protein drop that is from about 10 to 50 μL. Higher volumes of protein solution can be used, but greater volumes may adversely affect the diffusion gradient within the capillary. Optionally, agarose can be added to the protein sample at a low concentration. Agarose decreases the convective mass transport within the capillary, helps to avoid slippage of the crystal during initial screening, and facilitates nucleation.

Figure 7A:
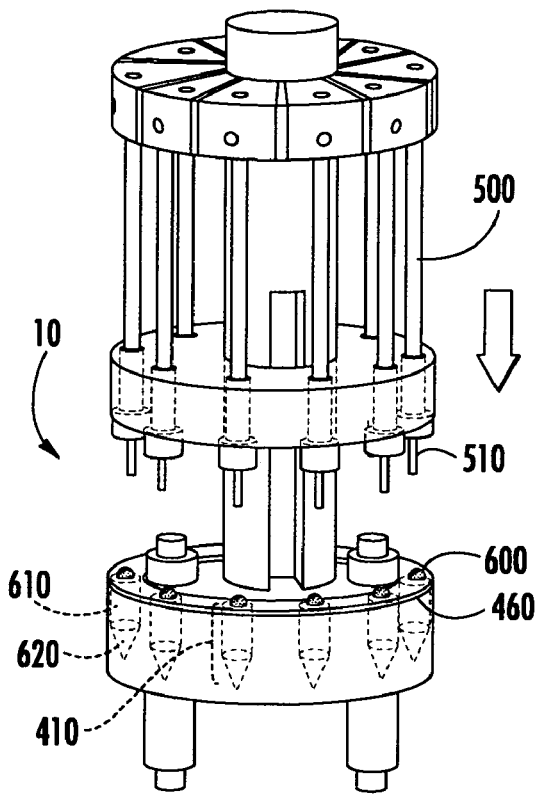
FIG. 7a is a perspective view of the cassette being assembled for use and having protein drops deposited on the lower member.

With reference to FIGS. 7a through 7g, the loading and use of the cassette is illustrated. FIG. 7a depicts a fully loaded cassette being assembled. As shown in FIG. 7a, a sealant 620 is in the lower portion of the cavity 410, the upper portion is filled with the desired precipitating solutions 610, the cavities are sealed with the pierceable layer 460, and a protein drop 600 has been deposited on the pierceable layer above each cavity.

Figure 7B:
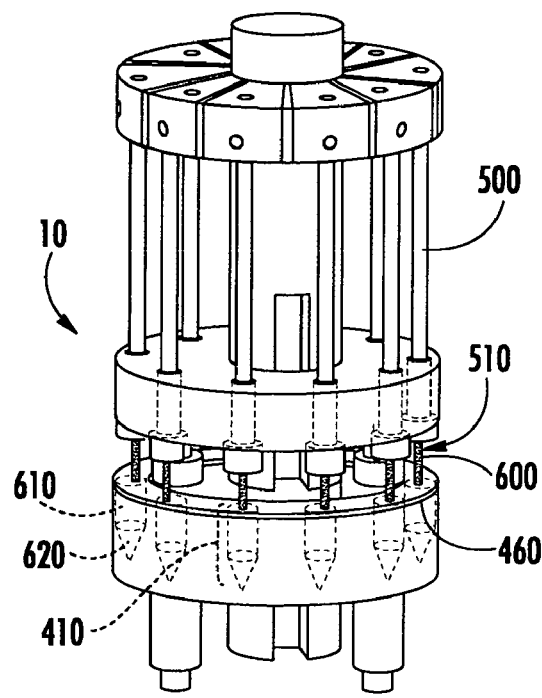
FIG. 7b is a perspective view of the cassette shown in FIG. 7a that has been assembled for use and is taking protein solution into the capillary tubes.
Figure 7C:
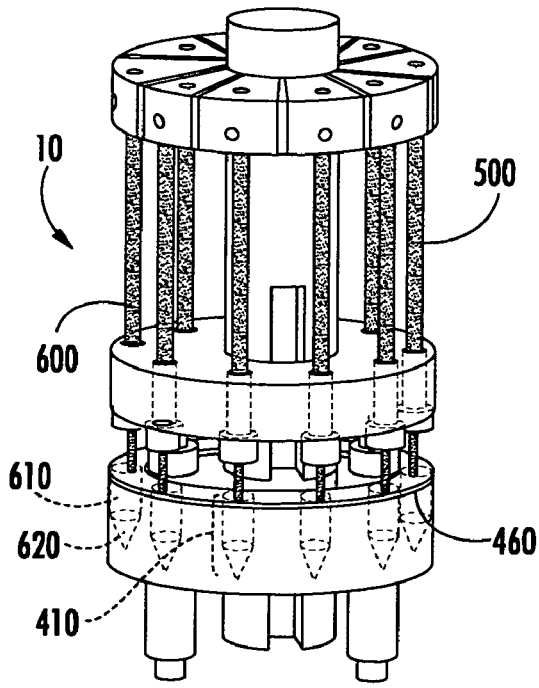
FIG. 7c is a perspective view of the cassette shown in FIG. 7b having the capillary tubes filled with protein solution.
Figure 7D:
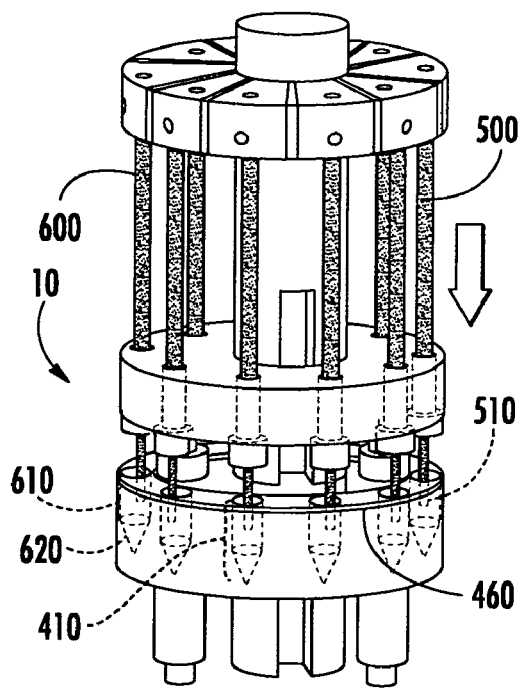
FIG. 7d is a perspective view of the cassette shown in FIG. 7c having the capillary tubes filled with protein solution and illustrating the capillary tubes penetrating the pierceable layer so that the tips are in contact with the precipitating solutions.

FIGS. 7b and 7c illustrates the protein solution entering and filling the capillary tubes. Capillary action takes the protein solutions into the capillaries. In FIG. 7d the top section of the cassette is moving downwardly towards the lower member so that the capillary tips 510 penetrate the pierceable layer 460 and contact the precipitating solutions 620.

Although the figures illustrate the cassette in a vertical orientation during the soaking process, crystallization is best performed in the horizontal orientation. The cassette uses counter-diffusion to create a supersaturation wave as the solutions diffuse against each other. In a vertical orientation any crystals that are formed would have a tendency to fall downward in the capillary disrupting any concentration gradients as well as mixing different crystals.

Figure 7E:
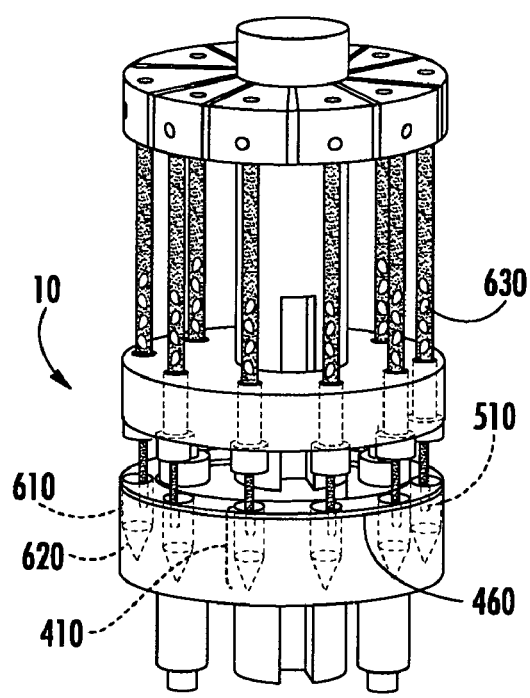
FIG. 7e is a perspective view of the cassette shown in FIG. 7d illustrating protein crystallization as the precipitation solution diffuses across the capillary tubes.

FIG. 7e illustrates that as the precipitating solution diffuses across the protein solution a supersaturation wave is formed and protein crystals 630 begin to form. When the precipitating solution (salt solution) contacts the protein solution, a liquid-liquid free-diffusion system is formed activating a super saturation wave along the capillary. This gradient is a result of the salts initially diffusing into the protein solution, forming a salt gradient of high concentration near the protein-precipitating interface and falling to a lower concentration as it moves across the capillary. As a result of the gradient, crystallization conditions are not uniform throughout the capillary and crystals of varying quality and size will be produced. Thus, one advantage of the cassette is that multiple crystallization conditions are present in a single capillary tube.

With time, the protein and precipitating solutions equilibrate. Single crystals are typically readily observable within 3 to 7 days of equilibration. The crystals should be sufficiently cryoprotected within 1 to 4 weeks of equilibration depending on the cryoprotectant and protein solutions.

Figure 7F:
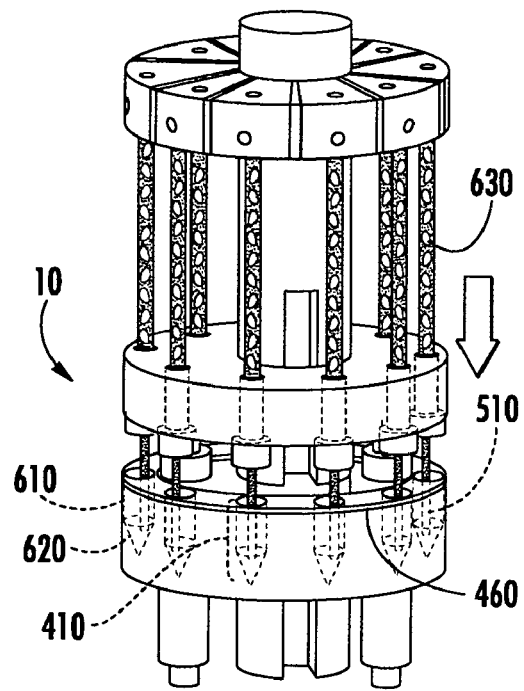
FIG. 7f is a perspective view of the cassette shown in FIG. 7e illustrating the step of sealing the capillary tubes by contacting the capillary tips with the sealant.
Figure 7G:
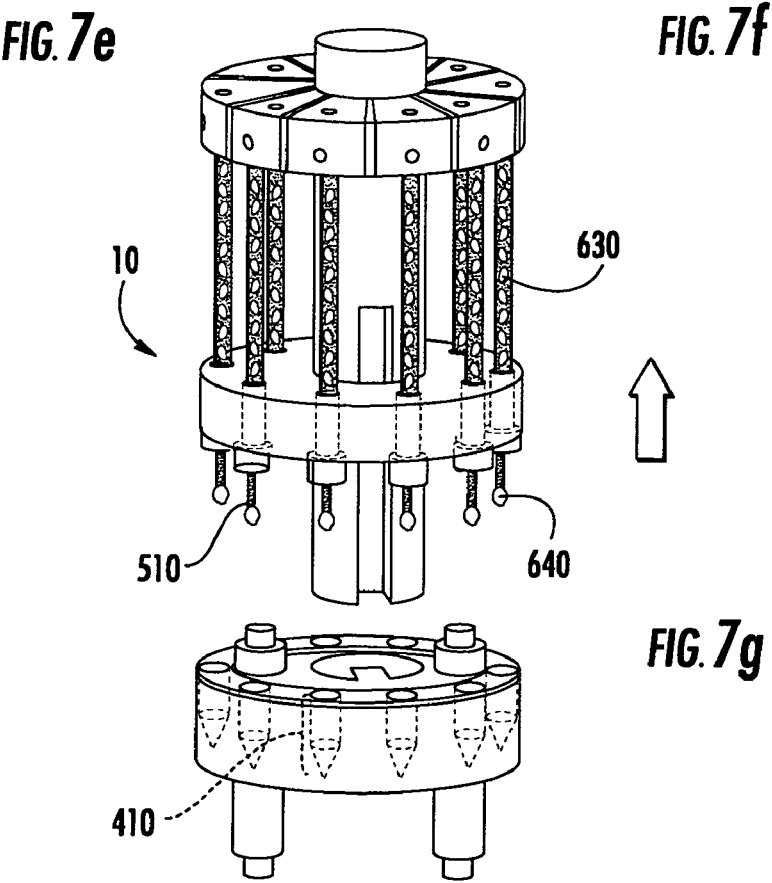
FIG. 7g is a perspective view of the cassette shown in FIG. 7f having sealed capillary tubes.

With reference to FIG. 7f, the step of sealing the capillaries is illustrated. As FIG. 7f illustrates, the top section of the cassette is pushed towards the lower member until the capillary tips contact the sealant 620. In this regard, FIG. 7g illustrates capillary tips 510 that have been sealed with the sealant 640. After the capillaries are sealed, the top section is removed from the lower member and transferred to an X-ray diffractometer for initial screening and data collection.

The cassette's design is particularly suited for attaching it to a cassette positioning system. In the cassette positioning system, the cassette is attached to a rotating adaptor that positions each capillary tube in front of an X-ray beam for diffraction analysis. The cassette positioning system is capable of rotating the cassette about both the x-axis and y-axis. At the rotation stage, the cassette is mounted so that its shaft is aligned in the x-axis. After mounting the cassette in the rotating adaptor, an automated mechanism indexes to a particular capillary so that the capillary is aligned parallel to the X-ray beam. Next, the automated system slides the middle member towards the upper member until the ferrels are disengaged from the middle member. A capillary tube is extended outwardly from the cassette until it is parallel to the y-axis of rotation and is placed in alignment with an X-ray beam source.

The cassette rotation stage is disposed beneath a Y-Z translation stage called the cassette scan stage. The cassette scan stage translates the cassette so that the X-ray beam moves up and down the capillary. As a result, the cassette positioning system is capable of moving up and down in a direction that is parallel to the y-axis of rotation. This allows a particular crystal in the outwardly extended capillary to be aligned with the X-ray beam.

The Y-Z translation stage (the capillary scan stage) is disposed beneath an X-Z translation stage called the eccentricity correction stage. This stage centers the crystal in the X-ray beam.

The final stage is called the capillary rotation stage. The capillary rotation stage rotates the entire system, including the outwardly extended capillary tube about the y-axis. The capillary rotation stage is a turntable that is disposed above the other stages and is joined to the eccentricity correction stage such that the system and cassette are suspended downwardly from the turntable or any orientation that best adapts to the particular X-ray source. The assembly is mounted on the turntable such that the center of the capillary is aligned with the turntable's center of rotation.

The cassette positioning system uses computer-controlled microsteppers to translate and rotate the capillary through the X-ray beam. During initial screening experiments, the cassette scan stage will translate the capillary through the X-ray beam, pausing in steps. At each step the eccentricity correction stage translates the capillary back and forth across the beam to screen for high quality crystals. During this step, the scattered X-ray intensity of reflections over the background noise (I/sigma) within a specific range of resolution is measured (usually reflection spots having I/sigma measurements greater than 3 are preferred). The quality of each crystal will be the evaluation by their I/sigma, mosaicity of reflection spots and diffraction limit (greater than 3 Angstroms). If no high quality crystals are found, the cassette positioning system advances the cassette to the next capillary and the process is repeated.

If a crystal having sufficient quality for X-ray analysis is detected, the targeted crystal is positioned in the center of the X-ray beam and the axis of rotation for the turntable runs through the crystal's center. The capillary can then be subjected to super-cooling by a direct cryogenic gas flow to freeze the crystal. The targeted crystal can then undergo a series of diffraction at incremented angular oscillations until a complete data set is obtained. Usually a 90 degree sweep in steps of 1 degree is sufficient to collect a complete data set for high symmetry crystals. Once the analysis is complete, the capillary is returned to its beginning position within the cassette and the cassette is rotated about the x-axis until the next capillary is aligned with the X-ray beam. At this time, the process is repeated until all capillary tubes have been analyzed.

The cassette's features make it particularly suited for high-throughput protein crystallization. Robotic automated systems could be used to take the cassette through multiple operations making it possible to perform tests on thousands of samples simultaneously. Numerous lower members could be manufactured and pre-loaded with varying precipitation solutions. This would allow a researcher to select and purchase lower members that are ready for installation onto the shaft without requiring the need to transfer solutions to the cassette. The cassette is adaptable to a robotic system that could deposit a predetermined amount of protein solutions on the lower member's surface, load the lower member onto the shaft, and take the cassette through the steps necessary for protein crystallization by repositioning the lower member on the shaft at predetermined time intervals. After completing the protein crystallization steps, the automated system transfers the cassette to an X-ray diffractometer for analysis and data collection.

The advantage of the crystallization cassette is that it simultaneously combines the processes of protein crystallization, high X-ray scattering atom incorporation, and cryoprotection. This allows the crystals to remain in a stable environment at all times and eliminates the need for physical manipulation or exposing the crystals to drastic chemical changes. After crystal growth is completed the crystals can be quickly evaluated in situ without ever having to remove them from their original growth environment.

Figure 8A:
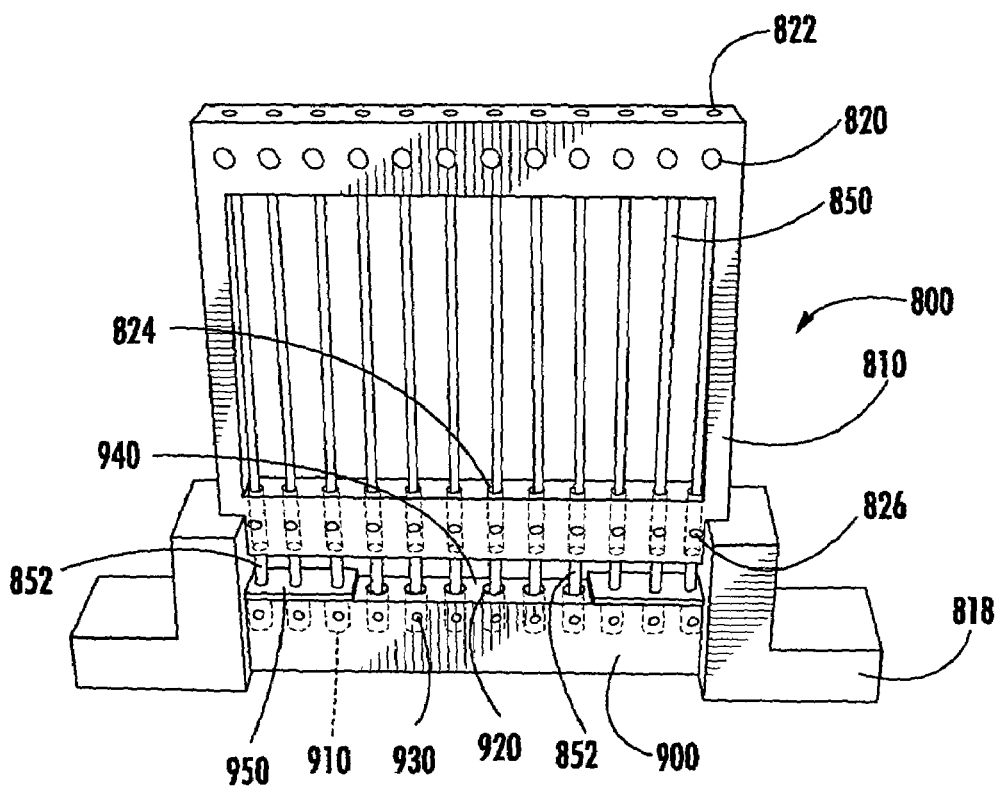
FIG. 8a is a perspective side view of a second form of the crystallization cassette.
Figure 8B:
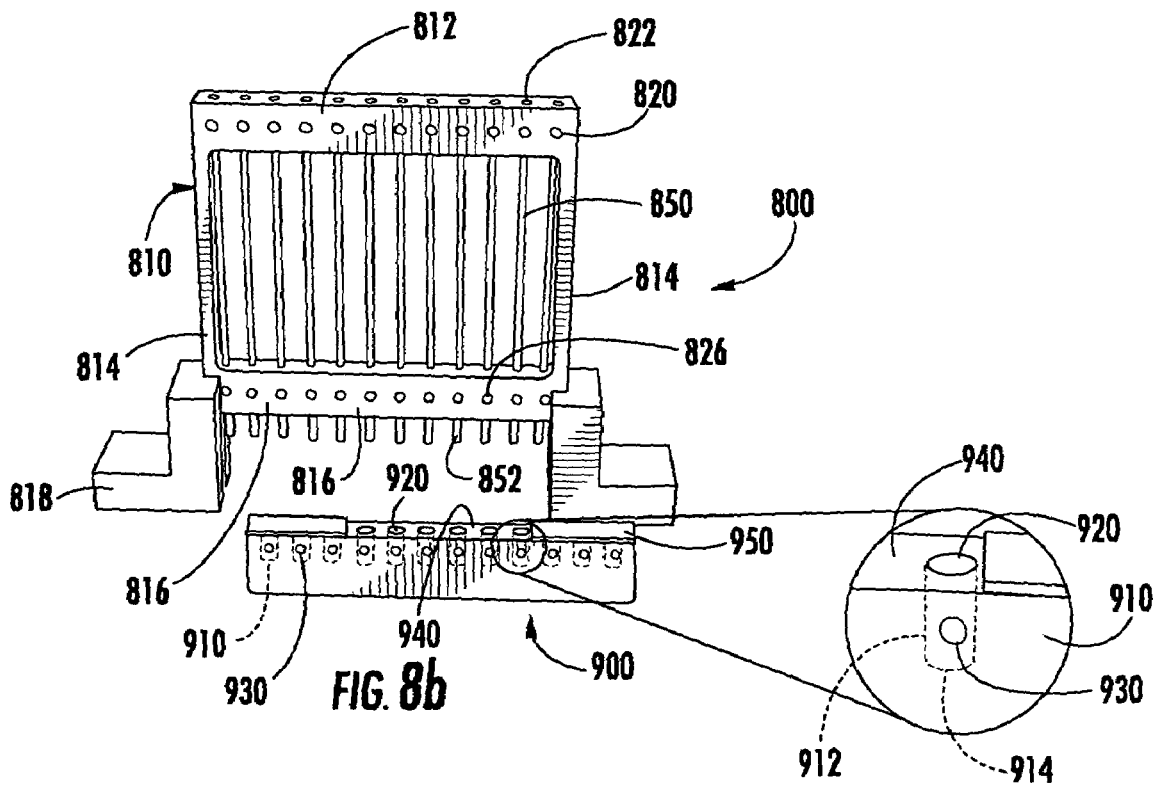
FIG. 8b is a perspective view of the cassette shown in FIG. 8a having the precipitating reservoir member separated from the support member.

With reference to FIGS. 8a and 8b, a second embodiment of the crystallization cassette 800 is illustrated. The cassette has a support member 814, a housing member 812 joined to the top portion of the support member, a stabilizing member 816 joined to the middle portion of the support member, and a precipitating reservoir member 900 (reservoir) that is joined to the support member's bottom portion, and a plurality of capillary tubes 850 that extend downwardly from the housing member through passageways 824 disposed in the stabilizing member.

The capillaries' distal ends (tips) 852 extend through the passageways and downwardly below the stabilizing member. In this regard, FIGS. 8a and 8b illustrate the capillary tips extending below the stabilizing member. Optionally, the support member has a pair of feet 818 that help stabilize the cassette 800.

The reservoir member 900 has a plurality of cavities 920 on the surface 940 facing the capillary tubes. Each cavity is aligned with and corresponds to a single capillary tube. The cavities, similar to the cavities discussed above, are reservoirs for the sealant layer and the precipitating solutions.

The methods for using the first 10 and second cassette 800 are substantially the same. Both cassettes use the counter-diffusion technique to combine the four protein crystallization steps. With reference to the method for using the cassette 800, the bottom portion 914 of the reservoir member is filled with a sealant, such as clay or wax. Next, A precipitating solution is added to the upper portion 912 of the cavity. Placing a pierceable layer 950 over the cavities seals the cavities. A drop of protein solution is then deposited on the pierceable layer above each cavity.

After completing the initial loading, the reservoir member 900 is slid onto the support member and slid upwardly until the capillary tips contact the protein sample. Capillary action takes the protein solution into the capillary tubes. After an effective amount of time has passed for the protein solution to fill the capillaries, the reservoir member is slid upwardly until the capillary tips penetrate the pierceable layer and contact the precipitating solutions. The precipitating solutions and protein solution counter-diffuse against each other until equilibration is reached. After crystal formation and a sufficient amount of time has passed to cryoprotect the crystals and to incorporate scattering atoms into the protein crystals the capillaries are removed for X-ray analysis.

As should be evident from the foregoing discussion, the crystallization cassette is a beneficial tool to a crystallographer. The cassette's design facilitates testing multiple precipitating solutions and crystallization conditions simultaneously. Its compact size and restricted geometry make the cassette adeptly suited for easy transport and high-throughput crystallization processes. The cassette is adaptable to automated processes from the initial crystallization steps to the analysis procedures performed on an X-ray diffractometer. As such, the cassette is a valuable tool that will aid crystallographers in deciphering and solving the structures for thousands of proteins.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A crystallization cassette comprising:
   a support member having a top, middle, and bottom portion;
   a housing member joined to the top portion;
   a stabilizing member joined to the middle portion having a plurality of capillary passageways;
   a precipitating reservoir member joined to the bottom portion, whereby the capillary tubes are in fluid communication with the precipitating reservoir; and
   a plurality of capillary tubes each having a proximal and distal end, wherein the capillary tubes' proximal ends are each joined to the housing member, and wherein each capillary tube extends downwardly from the housing member through a capillary passageway.

2. A crystallization cassette according to claim 1, wherein the precipitating reservoir member includes:
   a surface facing the distal ends of the capillary tubes; and
   a plurality of cavities on the surface, wherein each cavity respectively corresponds to a capillary tube.

3. A crystallization cassette according to claim 1, wherein the capillary tubes are suitable for X-ray diffraction.

4. A crystallization cassette according to claim 1, wherein the capillary tubes are selected from the group consisting of quartz, acrylic poly(methly methacrylate), polystyrene, mylar polycarbonate, CR 39, copolymers of styrene and poly(methly methacrylate), and their derivatives, and combinations thereof.

5. A crystallization cassette according to claim 4, wherein the capillary tubes are quartz.

6. A crystallization cassette according to claim 1, wherein the capillary tubes have a diameter from about 0.05 to 1 mm.

7. A crystallization cassette according to claim 1, wherein the capillary tubes have a diameter about 0.3 mm or less.

8. A crystallization cassette according to claim 1, wherein the support member is a shaft.

9. A crystallization cassette according to claim 2, wherein the precipitating reservoir member further includes a pierceable layer on the surface.

10. The crystallization cassette according to claim 9, wherein the pierceable layer is selected from the group consisting of latex, wax, plastic plug, agarose, and fracture ease.

11. The crystallization cassette according to claim 2, wherein the plurality of cavities each have a volume from about 5 to 50 µL.

12. A crystallization cassette comprising:
    a shaft having a top, middle, and bottom portion;
    an upper member joined to the top portion of the shaft;
    a middle member proximate to the middle portion of the shaft including:
       a first channel for receipt of the shaft; and
       a plurality of capillary passageways that are substantially parallel to the shaft and extend longitudinally through the middle member;
    a plurality of capillary tubes each having a proximal and distal end, wherein the capillary tubes extend downwardly from the upper member, and wherein each capillary tube extends downwardly through a capillary passageways; and
    a lower member proximate to the lower portion of the shaft having
       a first surface having a plurality of cavities located on the surface, wherein each cavity is in alignment and corresponds to a capillary tube,
       a second surface, opposite the first surface, and
       a second channel for receipt of the shaft, whereby the capillary tubes are in fluid communication with the lower member.

13. The crystallization cassette according to claim 12, wherein the shaft has a vertical axis extending from the lower member to the upper member and a keyway extending longitudinally along the axis.

14. The crystallization cassette according to claim 13, wherein the lower member has a key disposed in the second channel such that the key is adapted to slide along the keyway.

15. The crystallization cassette according to claim 13, wherein the middle member has a key disposed in the first channel such that the key is adapted to slide along the keyway.

16. The crystallization cassette according to claim 12, wherein the upper member includes a plurality of independently pivotable capillary housing sections, wherein each pivotable housing section is joined to the proximal end of a capillary tube and has a hinge disposed proximate to the shaft, and wherein the pivotable housing section is adapted to pivot upwardly such that the capillary tube is extended outwardly.

17. The crystallization cassette according to claim 16, wherein the outwardly extended capillary is substantially perpendicular to the vertical axis of the shaft.

18. The crystallization cassette according to claim 12, wherein the middle member has an outer edge that is parallel to the vertical axis, the outer edge having a plurality of channels that extend laterally through the middle member from the outer edge to the plurality of passageways such that a capillary tube is reversibly insertable through the channel into the passageway.

19. The crystallization cassette according to claim 12, wherein the capillary tube has a ferrel disposed proximate to the distal end.

20. The ferrel according to claim 19, having a substantially circular body with a lower and upper portion, and a base rim disposed at the lower portion having a diameter larger than the body.

21. The ferrel according to claim 20, having a beveled edge disposed at the upper portion.

22. The crystallization cassette according to claim 19, wherein the diameter of the passageways are the same or larger than the diameter of the body and smaller than the diameter of the rim such that as the middle disc is slid downwardly along the shaft the bodies of the ferrels will slide into the passageways.

23. The crystallization cassette according to claim 12, wherein the first channel is disposed at the center of the middle member.

24. The crystallization cassette according to claim 12, having a positioning lock for holding the middle member stationary relative to the shaft including:
 a positioning channel extending laterally through the middle member from the outer edge to the first channel;
 a positioning recess on the shaft that is perpendicular to the vertical axis and is aligned with the positioning channel; and
 a positioning pin that is reversibly insertable into the positioning channel such that as the middle member is slidably moved along the shaft the positioning pin can be inserted through the positioning channel into the positioning recess to thereby lock the middle member's position.

25. The crystallization cassette according to claim 12, wherein the lower member has a pierceable layer disposed on the first surface.

26. The crystallization cassette according to claim 25, wherein the pierceable layer is selected from the group consisting of latex, wax, plastic plugs, agarose, and fracture ease.

27. The crystallization cassette according to claim 12, wherein the plurality of cavities each have a volume from about 5 to 50 µL.

28. The crystallization cassette according to claim 12, wherein the lower member has a first depth control member for controlling the depth to which the capillary tubes are inserted into the cavities.

29. The crystallization cassette according to claim 28, wherein the first depth control member is a stud extending outwardly from the first surface in a direction that is substantially parallel to the vertical axis of the shaft.

30. The crystallization cassette according to claim 28, wherein the lower member's orientation to the shaft is inverted so that the second surface is facing the middle member.

31. The crystallization cassette according to claim 28, wherein the lower member has a second depth controlled member on the second surface for controlling the distance between the distal ends of the capillaries and the second surface.

32. The crystallization cassette according to claim 31, wherein the depth control member is a second stud having a height that is greater than the height of the first depth control member, and wherein the second stud extends outwardly from the second surface in a direction that is substantially parallel to the vertical axis of the shaft.

33. The crystallization cassette according to claim 12, wherein the second channel is disposed at the center of the lower member.

34. The crystallization cassette according to claim 12, wherein the capillary tubes are suitable for X-ray diffraction.

35. The crystallization cassette according to claim 12, wherein the capillary tubes are selected from the group consisting of quartz, acrylic poly(methly methacrylate), polystyrene, mylar polycarbonate, CR 39, copolymers of styrene and poly(methly methacrylate), and their derivatives and combinations thereof.

36. The crystallization cassette according to claim 12, wherein the capillary tubes are quartz.

37. The crystallization cassette according to claim 12, wherein the capillary tubes diameters are from about 0.05 mm to 1 mm.

38. The crystallization cassette according to claim 12, wherein the capillary tubes diameters are about 0.3 mm or less.

39. The crystallization cassette according to claim 12, wherein the upper, middle, and lower members are disc shaped.

40. The crystallization cassette according to claim 12, wherein the cassette has 12 capillary tubes.

41. The crystallization cassette according to claim 12, wherein the overall shape of the cassette is cylindrical.

42. The crystallization cassette according to claim 12, wherein the shaft, upper member, and lower member are comprised of an amorphous non-refractive plastic.

43. The crystallization cassette according to claim 12, wherein the cassette is made from a material selected from the group consisting of quartz, acrylic poly(methly methacrylate), polystyrene, mylar polycarbonate, CR 39, copolymers of styrene and poly(methly methacrylate), and their derivatives and combinations thereof.

44. A crystallization cassette according to claim 12, wherein the plurality of cavities each respectively have a lower portion and an upper portion.

45. A crystallization cassette according to claim 44, having a pre-loaded lower member comprising:
 a capillary sealant disposed in each cavities' lower portion;
 a precipitating solution, cryoprotectant solution, and a high X-ray scattering atom component disposed in the cavities upper portion; and
 a pierceable member disposed on the first surface such that the cavities are sealed.

46. A crystallization cassette according to claim 45, wherein the cavity sealant is selected from the group consisting of wax and clay.

47. A crystallization cassette according to claim 45, wherein the precipitating solution is selected from the group consisting of salts and alcohols.

48. A crystallization cassette according to claim 45, wherein the cryoprotectant solution is selected from the group consisting of primary alcohols, glycerol, polyethylene glycol, methylpentanediol, and derivatives thereof.

49. A crystallization cassette comprising:
 a shaft having a top, middle, and bottom portion;
 a capillary housing member joined to the top portion of the shaft;
 a capillary stabilizing member joined to the middle portion of the shaft having a first channel that is adapted for slidably receiving the shaft, and a plurality of passageways that are parallel to the vertical axis of the shaft and extend longitudinally through the stabilizing member;

a plurality of capillary tubes having a proximal and distal end, wherein the capillary tubes extend downwardly from the housing member, and wherein each capillary tube extends downwardly through one of the passageways; and a precipitation reservoir member joined to the lower portion of the shaft having a surface facing the stabilizing member, a plurality of cavities located on the surface, wherein each cavity is in alignment and corresponds to a capillary tube, and a second channel that is adapted for slidably receiving the shaft.

50. A method of growing biological crystals comprising the steps of:
 a. providing a crystallization cassette as described in claim 45 having a pro-loaded lower member;
 b. depositing a protein solution on the pierceable layer above each cavity;
 c. repositioning the lower member along the shaft until the distal ends of the capillary tubes contact the protein solutions;
 d. diffusing the protein solutions into the capillary tubes;
 e. piercing the pierceable layer with the distal end of the capillary tubes by repositioning the lower member towards the middle member;
 f. contacting the distal ends of the capillary tubes with the precipitating solutuion, cryoprotectant solution, and scattering atom component;
 g. diffusing the precipitating solution, cryoprotectant solution, and scattering atom component into the capillary tubes;
 h. growing biological crystals in the capillary tubes;
 i. sealing the distal ends of the capillary tubes with the capillary sealant; and
 j. selecting crystals for X-ray diffraction.

51. The method for growing biological crystals according to claim 50, wherein the step of providing a pre-loaded loaded member further comprises the steps of:
 a. inserting a capillary sealant within the cavities;
 b. inserting precipitating, cryoprotectant, and scattering atom solutions into each of the cavities; and
 c. sealing the cavities with a pierceable layer.

52. The method for growing biological crystals according to claim 50, further comprising the step of analyzing the crystals in situ.

53. The method for growing biological crystals according to claim 52, wherein the step of analyzing crystals in situ further comprises the steps of:
 a. mounting the cassette in an X-ray diffractometer on a motorized adaptor for rotating the cassette;
 b. extending a capillary tube outwardly from the cassette;
 c. applying a stream of cryogenic gas to the capillary tube;
 d. applying an X-ray beam to a desired location on the extended capillary tube;
 e. rotating the capillary in the X-ray beam; and
 f. collecting x-ray data.

54. The method for growing biological crystals according to claim 50, wherein the biological crystal is selected from the group consisting of proteins, nucleic acids, and viruses.

55. The method for growing biological crystals according to claim 50, wherein the volume of protein solution and precipitating solution are about a 1:1 ratio.

56. A cassette positioning system for rotating a crystallization cassette about an x-axis and y-axis comprising:
 an X-ray source;
 a turntable for rotating the cassette about the y-axis of rotation;
 an eccentricity correction stage disposed below the turntable;
 a capillary scan stage disposed under the eccentricity stage; and
  a cassette rotation stage for rotating a the cassette about the x-axis.

57. A method of growing and analyzing macromolecules comprising:
 providing a plurality of capillary tubes each having a first and second end;
 contacting the second end of each capillary tube to a solution having a solvated macromolecule therein;
 diffusing the solution into the capillary tubes;
 inserting the second end of each capillary tube into a corresponding cavity having one or more precipitating agents therein;
 allowing the one or more precipitating agents to counter-diffuse against the solution in each capillary tube;
 allowing macromolecule crystals to grow in the capillary tubes; and
 analyzing the crystals in situ via x-ray diffractometry.

58. The method according to claim 57, further comprising sealing the second end of each capillary tube.

59. The method according to claim 57, wherein the macromolecule comprises a protein.

60. The method according to claim 57, wherein the precipitating agent further comprises a cryoprotectant solution, scattering atom component, or combination thereof.

61. The method according to claim 57, further comprising disposing a pierceable layer between the solution and each corresponding cavity, and wherein the solution is in the form of a droplet.

62. The method according to claim 61, wherein the step of inserting the second end of each capillary tube into a corresponding cavity further comprises piercing the pierceable layer with the second end of each capillary tube.

* * * * *

UNITED STATES PATENT AND TRADEMARK OFFICE
CERTIFICATE OF CORRECTION

| | | |
|---|---|---|
| PATENT NO. | : 7,118,626 B2 | Page 1 of 1 |
| APPLICATION NO. | : 10/651499 | |
| DATED | : October 10, 2006 | |
| INVENTOR(S) | : Ng et al. | |

It is certified that error appears in the above-identified patent and that said Letters Patent is hereby corrected as shown below:

<u>Column 14,</u>

Line 4, after "0.05", insert --mm.--.

<u>Column 17,</u>

Line 20, "pro-loaded" should read --pre-loaded--.

Signed and Sealed this

Twentieth Day of March, 2007

JON W. DUDAS
*Director of the United States Patent and Trademark Office*